United States Patent
Davis et al.

(10) Patent No.: US 9,304,018 B2
(45) Date of Patent: Apr. 5, 2016

(54) BODY SHAPE, POSITION, AND POSTURE RECOGNITION SUIT WITH MULTI-CORE OPTICAL SHAPE SENSING FIBER

(71) Applicant: INTUITIVE SURGICAL OPERATIONS, INC., Sunnyvale, CA (US)

(72) Inventors: Matthew A. Davis, Christiansburg, VA (US); Eugene Malinowski, Christiansburg, VA (US); Jason L. Chevalier, Christiansburg, VA (US); Alaina M. McGregor, Blacksburg, VA (US); Matthew Reaves, Baltimore, MD (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 14/531,416

(22) Filed: Nov. 3, 2014

(65) Prior Publication Data
US 2015/0124266 A1    May 7, 2015

Related U.S. Application Data

(60) Provisional application No. 61/899,966, filed on Nov. 5, 2013.

(51) Int. Cl.
| | |
|---|---|
| *G01B 11/24* | (2006.01) |
| *G01D 5/353* | (2006.01) |
| *A61B 5/107* | (2006.01) |
| *A61B 5/11* | (2006.01) |
| *A61B 5/00* | (2006.01) |

(52) U.S. Cl.
CPC .......... *G01D 5/35367* (2013.01); *A61B 5/1079* (2013.01); *A61B 5/1116* (2013.01); *A61B 5/6804* (2013.01); *G01D 5/3538* (2013.01); *A61B 2562/0266* (2013.01); *Y10T 29/49* (2015.01)

(58) Field of Classification Search
USPC ........... 356/614, 73.1; 606/130, 1, 10, 13, 15, 606/41, 42; 600/104, 106, 145, 483, 587, 600/595; 385/13, 12
See application file for complete search history.

(56) References Cited

U.S. PATENT DOCUMENTS

| | | | | |
|---|---|---|---|---|
| 5,701,370 | A * | 12/1997 | Muhs et al. ..................... | 385/13 |
| 6,071,279 | A * | 6/2000 | Whayne et al. ................. | 606/41 |
| 7,930,065 | B2 * | 4/2011 | Larkin et al. .................. | 700/245 |

(Continued)

OTHER PUBLICATIONS

Joint Motion Measurement, Training Circular TC 8-640, Headquarters—Department of the Army, Washington, DC, Apr. 24, 1987, 79 pages.

*Primary Examiner* — Sang Nguyen

(57) ABSTRACT

A measurement apparatus includes a body suit for a body that includes an appendage having a pivotable joint, the body suit comprising a sleeve to cover the appendage, wherein a first portion of the sleeve is configured to cover the pivotable joint. One or more multi-core optical fiber sensors is/are within or on the sleeve in a routing pattern that is substantially aligned with a longitudinal axis of the sleeve except within the first portion and that is at least partially transverse to the longitudinal axis within the first portion. An optical shape sensing system coupled to the one or more multi-core optical fiber sensors sends light into the one or more multi-core optical fiber sensors and determines a position of each of the multiple appendages based on reflected optical signal measurements detected from one or more multi-core optical fiber sensors.

18 Claims, 14 Drawing Sheets

(56) References Cited

U.S. PATENT DOCUMENTS

| | | | |
|---|---|---|---|
| 8,347,738 B2 * | 1/2013 | Tung et al. | 73/862 |
| 8,439,844 B2 * | 5/2013 | O'Rourke | 600/483 |
| 8,773,650 B2 * | 7/2014 | Froggatt et al. | 356/73.1 |
| 9,084,624 B2 * | 7/2015 | Larkin et al. | |
| 2004/0106872 A1 * | 6/2004 | Kosuda | 600/485 |
| 2010/0144490 A1 * | 6/2010 | Purdy et al. | 482/1 |

* cited by examiner

Movement was chosen to mimic natural motion. Fiber in a stiff package moved out of the sleeve distance shown By running the fiber
through the joints
horizontally nearly all
movement was removed

| Test Matrix - Arm |||||| 
|---|---|---|---|---|---|
| Angle ID | Angle Name | test angle 'a' | test angle 'b' | test angle 'c' | Image |
| A1 | Shoulder Flexion/Extension | 188 | 60 | -34 | |
| A2 | Shoulder Lateral/Medial rotation | 124 | 60 | -7 | |

Figure 17A

| Test Matrix - Leg |||||| 
|---|---|---|---|---|---|
| Angle ID | Angle Name | test angle 'a' | test angle 'b' | test angle 'c' | Image |
| H1 | Hip Flexion | 113 | 55 | 0 | |
| H2 | Hip Adduction/Abduction (supine) | 120 | 80 | 37 | |

Figure 17B

BODY SHAPE, POSITION, AND POSTURE RECOGNITION SUIT WITH MULTI-CORE OPTICAL SHAPE SENSING FIBER

PRIORITY APPLICATION

This application claims priority from U.S. provisional application Ser. No. 61/899,966, filed on Nov. 5, 2013, the contents of which are incorporated herein by reference.

This invention was made with government support under Contract No. W900KK-13-C-0034 awarded by the Department of the Army. The government has certain rights in the invention.

TECHNICAL FIELD

The technology in this application relates to optical measurement apparatus and techniques.

BACKGROUND

Human posture recognition and the measurement of body shape and position is critical to industries that develop safety equipment, perform skeletal modeling, conduct athletic performance research, research physiological response to various environmental conditions, ergonomics, and the entertainment (both video and gaming) industry. These industries currently rely on manual measurements using rulers and goniometers (see, e.g., US Army Publication TC_8-640), systems with inertial measurement units (IMUs) and discrete bend sensors, or visual camera-based systems. All three of these types of systems have significant challenges with respect to accuracy, efficiency, and complexity.

Measurement made using hand tools are subject to human systematic errors in the selection of measurement points and can be very time consuming. Additionally, this type of a measurement does not provide the ability to capture dynamic events, greatly restricting its usefulness.

Systems incorporating discrete bend sensing or IMUs suffer from massive amounts of data that need to be processed in order to determine the angles of the joints of the body. Once processed, these data cannot achieve the needed accuracies required in the industry and other applications. These types of sensors typically add weight to the user which may restrict movements of the user. Further, these types of sensors are bulky and interfere with the sensing system which requires further correction to the measurements.

Optical imaging solutions provide a more comprehensive and non-invasive identification of body shape, position, and posture. However, there are many disadvantages to imaging based solutions. Primarily, imaging based solutions requiring line-of-sight to the body being measured. Environments and applications that include obstructions or debris fields such as smoke, extreme humidity, and fog increase the difficulty or prevent accurate measurements. Moreover, a system of multiple cameras at all angles from the test subject is needed to fully identify desired measureands. This typically limits the motion and position of the user to a small, predefined area. Further, the subject of interest must remain in the focal area of the measurement system for optimal performance. These measurement systems present logistical challenges as they are not easily transported, and they must be highly calibrated to produce accurate results.

What is needed by the industry is a solution that overcomes these challenges, is portable, does not require line of sight to operate, and is highly accurate.

SUMMARY

A measurement apparatus includes a body suit for a body that includes an appendage having a pivotable joint, the body suit comprising a sleeve to cover the appendage, wherein a first portion of the sleeve is configured to cover the pivotable joint. One or more multi-core optical fiber sensors is/are within or on the sleeve in a routing pattern that is substantially aligned with a longitudinal axis of the sleeve except within the first portion and that is at least partially transverse to the longitudinal axis within the first portion. An optical shape sensing system coupled to the one or more multi-core optical fiber sensors sends light into the one or more multi-core optical fiber sensors and determines a position of each of the multiple appendages based on reflected optical signal measurements detected from one or more multi-core optical fiber sensors.

In example embodiments, the optical shape sensing system is configured to determine a shape and/or a posture of the body based on reflected optical signals detected from one or more multi-core optical fiber sensors. In example embodiments, the optical shape sensing system is an optical frequency-domain reflectometry (OFDR) based system.

In example embodiments, a launch unit is coupled to a first end of each of the one or more multi-core optical fiber sensors. An orientation of the launch unit defines a coordinate frame for the optical shape sensing system measurements. The launch unit may include or may be coupled to an inertial measurement unit (IMU). In addition, the launch unit may include or may be coupled to a global positioning system (GPS).

In example embodiments, the routing pattern in the first portion is substantially transverse to the longitudinal axis of the sleeve. As one example implementation, the one or more multi-core optical fiber sensors is configured in or on the body suit to traverse across the one or more movable joints from a first side of the one or more movable joints to a second opposing side of the one or more movable joints.

In example embodiments, the one or more multi-core optical fiber sensors is configured in or on the body suit to traverse across the one or more movable joints with a predetermined, minimum bend radius associated with the one or more multi-core optical fiber sensors.

In example embodiments, the optical shape sensing system is configured to calibrate measurements detected from the one or more multi-core optical fiber sensors as configured in or on the body suit.

Another example embodiment of a measurement apparatus includes a body suit for a body that includes an appendage having a pivotable joint. The body suit includes a sleeve to cover the appendage, and a first portion of the sleeve is configured to cover the pivotable joint. One or more multi-core optical fiber sensors is/are within or on the sleeve in a routing pattern that is substantially aligned with a longitudinal axis of the sleeve except within the first portion and that is at least partially transverse to the longitudinal axis within the first portion. A connection terminal is configured to connect the one or more multi-core optical fiber sensors to an optical shape sensing system for sending light into the one or more multi-core optical fiber sensors and determining a position of each of the multiple appendages based on reflected optical signal measurements detected from the one or more multi-core optical fiber sensors.

Another example embodiment includes a method for making a body suit for a body that includes an appendage having a pivotable joint, where the body suit includes a sleeve to cover the appendage, and where a first portion of the sleeve is configured to cover the pivotable joint. The method includes a first step of routing one or more multi-core optical fiber sensors within or on the sleeve in a routing pattern that is substantially aligned with a longitudinal axis of the sleeve except within the first portion and that is at least partially transverse to the longitudinal axis within the first portion. A second step provides a connection terminal that is configured to connect the one or more multi-core optical fiber sensors to an optical shape sensing system for injecting light into the one or more multi-core optical fiber sensors and determining a position of one or more of the multiple appendages based on reflected optical signal measurements detected from one or more multi-core optical fiber sensors.

BRIEF DESCRIPTION OF THE FIGURES

FIGS. 17A and 17B show example range of motion test matrices.

DETAILED DESCRIPTION

Figure 1:
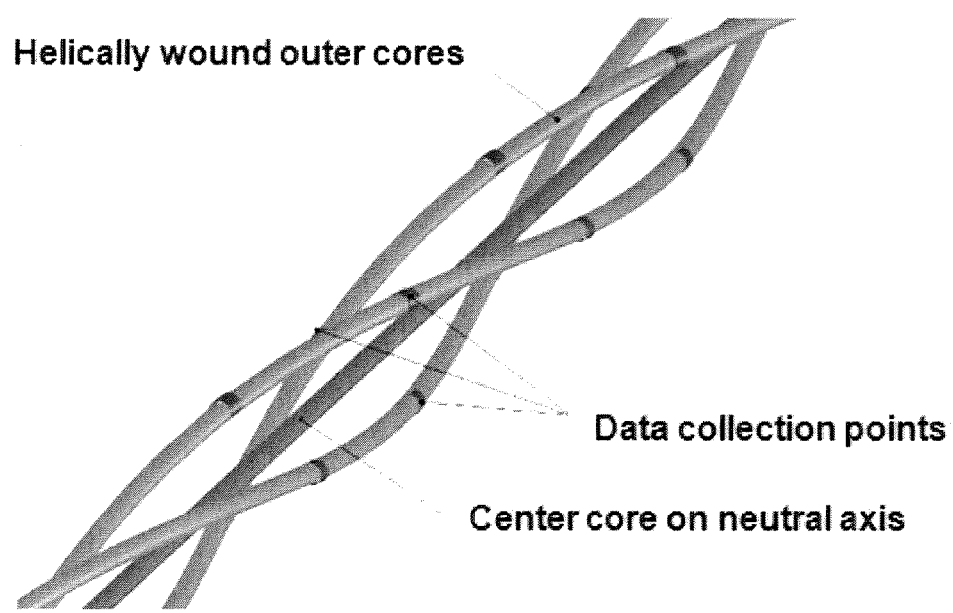
FIG. 1 shows an example fiber optic shape sensor which is a monolithic, multicore optical fiber with a center core along the neutral axis and three outer cores equidistant from the neutral axis that helix around the center core.

The inventors recognized that shape sensing fiber integrated into a tight fitting suit could be advantageously applied to the technology field of human posture recognition and measurement. They also realized that several challenges needed to be overcome to produce a functional human posture recognition and measurement system. Optical fiber based sensing systems have limitations that include sensitivity to shock and vibration, determination of a local and global coordinate system, the need of a continuous sensor path around the areas being measured (which is also a benefit as it provides dense data down the entire length) and maintaining a minimum bend radius. While all of these present significant challenges, they can be overcome by properly designing the sensor packaging and routing the sensors around the test subject through a tight fitting suit. The routing pattern should be specifically designed however to prevent sliding of the fiber at the joints and to prevent a pistoning and bunching effect as the appendages are moved. Pistoning is defined as the increase or decrease in the protrusion at the end of the sensor that results from the extension of the appendage. Carefully routing the fiber transversely across the joints can mitigate and remove this in many cases. Although the description below is in the context of human posture to provide a detailed, non-limiting example, the technology may also be applied to non-human bodies or shapes with flexible appendages and joints.

Fiber optic shape sensing is an application of distributed fiber optic strain sensing, which can be achieved through optical frequency-domain reflectometry (OFDR), Brillouin scattering, or other technology. OFDR provides extremely high spatial resolution compared to other techniques, which makes it ideal for fiber optic shape sensing. OFDR enables local measurements of shift in the reflection spectrum of a fiber optic at thousands of points per meter of fiber. Strain produces a shift in the scattering spectrum of a fiber optic sensor when the sensor experiences strain:

$$\Delta v \approx K_\epsilon \epsilon \qquad (1)$$

Here, $\Delta v$ is the measured spectral shift, $\epsilon$ is the applied strain, and $K_\epsilon$ is the strain-optic coefficient of the sensor. (Note that this expression ignores the effects of temperature changes to simplify this discussion.) Thus by using OFDR to obtain a distributed measurement of shifts in the scattering spectrum, one can scale this measurement strain through a straightforward calibration of the strain response $K_\epsilon$.

In an example OFDR system, light from a tunable laser source, which has a frequency scan rate, is launched into an interferometric interrogator, in which the incoming light is further split into two paths. The upper path is a reference path, and in the lower path, the light passes through a circulator before entering the sensing fiber. Along the length of the sensing fiber, small fractions of the incident light are reflected, either as a result of Rayleigh scatter or at distributed fiber Bragg gratings (FBGs) or discrete reflectors. The reflected light propagates back down the sensing fiber, through the circulator, and is recombined with the incident light from the reference path at a fiber optic coupler where the scattered light along the length of the sensing fiber interferes with light that has traveled along the reference path of the interferometric interrogator. A polarization beamsplitter (PBS) splits the light into two orthogonal polarization states, and the split interference pattern is detected independently at S and P photodetectors. A second interferometer within a laser monitor network measures fluctuations in the tuning rate as the light source scans through a frequency range. The laser monitor network also contains a gas cell which is used to provide absolute wavelength reference throughout the measurement scan.

A series of optical detectors convert detected light signals from the laser monitor network, gas cell, and the interference pattern from the sensing fiber into electrical signals for a data acquisition unit. A system controller data processor uses the acquired electrical signals from the data acquisition unit to extract a scattering profile along the length of the fiber sensor. More specifically, by applying a Fourier Transform, the frequency-domain OFDR data is converted into a complex-valued signal representing optical backscatter at finely-spaced delay intervals (e.g., equivalent to approximately 50 µm physical length per point) along the length of the fiber. A phase-based measurement of distributed strain is made for the sensing fiber to determine the distribution of scattered light along the length of the fiber. As mentioned above, this spatially-distributed backscatter can be generated either through Rayleigh scatter or from discrete or continuously-written FBGs. A preferred, example embodiment uses the fiber's Rayleigh scatter signature for OFDR-based sensing.

If a strain is imparted on the optical fiber, its Rayleigh scatter signature or FBG peak will shift in frequency. This frequency shift is linearly proportional to the applied strain. The applied strain results in a spectral shift in the OFDR signal which varies as function of delay. After converting to the delay domain, the spatially-varying frequency shift results in a phase slope which varies as a function of delay. The phase of the delay-domain OFDR signal is used to measure strain along the length of the optical fiber. This calculation is performed by comparing the fiber in a strained "measurement" state with OFDR data obtained from a "reference" state.

Example fiber optic shape sensors include a monolithic, multicore optical fiber with a center core along the neutral axis and three outer cores equidistant from the neutral axis, which helix around the center core. See FIG. 1. Strain is measured in all four cores of the sensor simultaneously. The separation of the outer cores from the neutral axis permits measurement of bend-induced strain in the outer cores, which alternate between states of tension and compression in a constant bend. The helixed nature of the outer cores also allows twist-induced strain to be deduced, where in twist constitutes a common strain in all of the outer cores which is nominally zero on the neutral axis (center core).

Equation (2) below shows the first order strain in the center core ($\epsilon_0$) and three outer cores ($\epsilon_1$, $\epsilon_2$, $\epsilon_3$), given a local configuration defined by axial tension ($\epsilon \downarrow z$), curvature vector (with components $\kappa_x^0$ and $\kappa_y^0$) and applied twist per unit length $$\frac{\Theta}{(L)}.$$

The transformation matrix depends on the outer core radius from the neutral axis a, the helix rate of the outer cores α, the angular positions of each outer core $\phi_i$, and Poisson's ratio ν. (For this analysis, the core radius is assumed to be the same for all outer cores, and the center core is assumed to be on the neutral axis. In practice, this cannot be assumed, but it is straightforward to generalize the matrix for non-ideal core geometries.) While the transformation matrix shown below is derived from a physical model, in practice this transformation matrix is deduced though a calibration procedure. Once the matrix is determined, it can be used to measure the fiber's configuration for any set of multicore strain measurements.

$$\begin{pmatrix} \epsilon_0 \\ \epsilon_1 \\ \epsilon_2 \\ \epsilon_3 \end{pmatrix} = \begin{bmatrix} 1 & 0 & 0 & 0 \\ \frac{1-v(a\alpha)^2}{1+(a\alpha)^2} & \frac{a(1-v(a\alpha^2))\sin(t+\phi_1)}{1+(a\alpha)^2} & \frac{-a(1-v(a\alpha)^2)\cos(t+\phi_1)}{1+(a\alpha)^2} & \frac{a^2\alpha}{1+(a\alpha)^2} \\ \frac{1-v(a\alpha)^2}{1+(a\alpha)^2} & \frac{a(1-v(a\alpha^2))\sin(t+\phi_2)}{1+(a\alpha)^2} & \frac{-a(1-v(a\alpha)^2)\cos(t+\phi_2)}{1+(a\alpha)^2} & \frac{a^2\alpha}{1+(a\alpha)^2} \\ \frac{1-v(a\alpha)^2}{1+(a\alpha)^2} & \frac{a(1-v(a\alpha^2))\sin(t+\phi_3)}{1+(a\alpha)^2} & \frac{-a(1-v(a\alpha)^2)\cos(t+\phi_3)}{1+(a\alpha)^2} & \frac{a^2\alpha}{1+(a\alpha)^2} \end{bmatrix} \begin{pmatrix} \epsilon_z^0 \\ \kappa_x^0 \\ \kappa_y^0 \\ \frac{\Theta}{L} \end{pmatrix}$$

Once the curvature and twist of the fiber are known at every point along the shape sensor, the shape of the fiber can be determined. As long as the location and orientation of the first measurement point is known well, knowledge of the curvature and twist allows the location and orientation of the adjacent point to be determined. This method is repeated at every measurement point to recreate the global shape of the fiber optic cable.

In practice, the fiber orientation of the first measurement point (known as the "launch region") is straight and well-controlled; its orientation defines the coordinate frame for the overall body shape measurement. In the present application, the launch region is affixed to an inertial measurement unit (IMU) which provides an initial measurement of the launch region orientation relative to a fixed lab frame. This is necessary to provide a fixed reference frame when the launch region is not stationary when the user is in motion.

Figure 2:
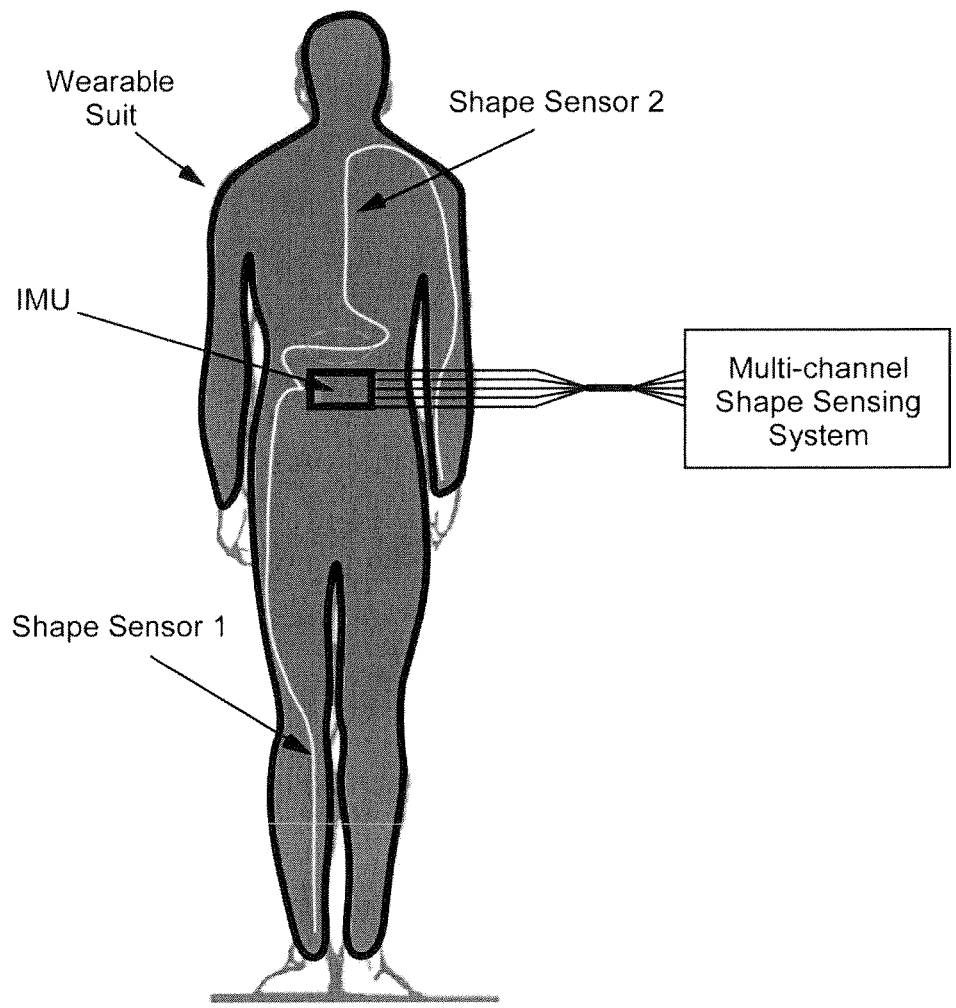
FIG. 2 illustrates an example wearable suit in which shape sensing fiber has been embedded to measure the position of several limbs position relative to an initial orientation provided by an IMU.

A shape sensing system, such as described in commonly-assigned U.S. Pat. No. 8,773,650 incorporated herein by reference, may be used to conduct the interrogation of a deployed sensing fiber. The shape sensing system is used to determine the position of a movable appendage using a fiber optic shape sensor attached to the movable appendage. A shape sensing system with multiple acquisition channels is preferably used to interrogate several shape sensing fibers used for the same and/or different appendages. FIG. 2 illustrates an example wearable suit in which shape sensing fiber has been embedded to measure the position of several human body appendages relative to an inertial measurement unit (IMU). Although shown and useable as a box separate from the suit, the multichannel shape sensing system may be constructed to be portable and carried by the individual, e.g., using a backpack, embedding in the suit, etc. A dashed oval is shown in FIGS. 2 and 3 to show a global reference straight section, e.g., a non-limiting example is shown.

Figure 3:
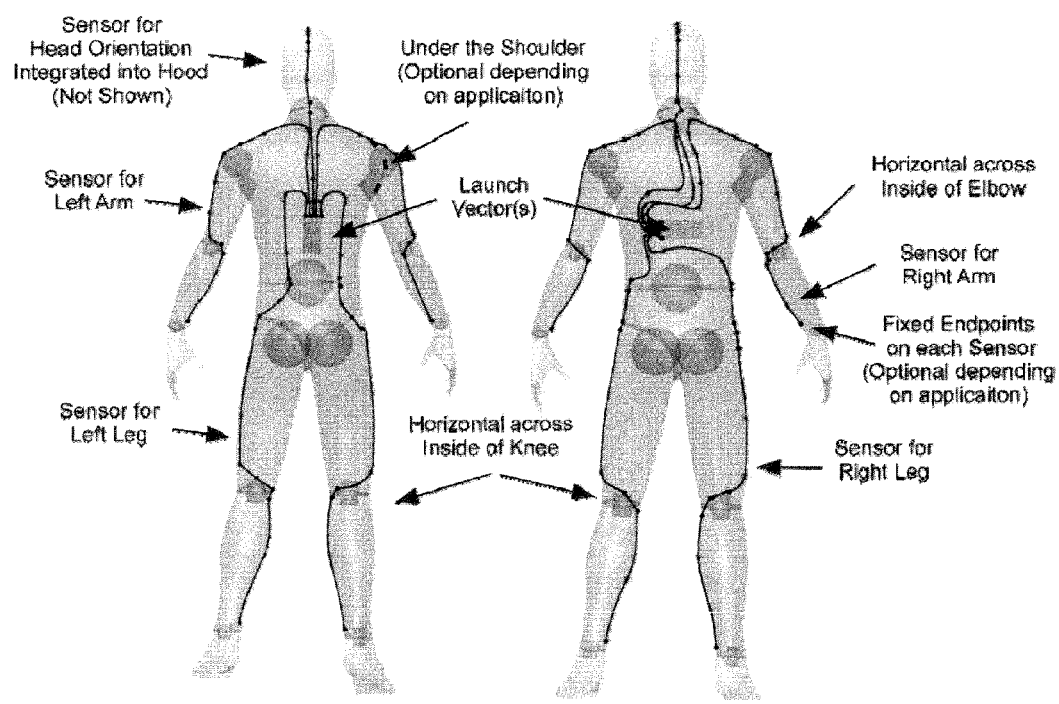
FIG. 3 illustrates schematically an example suit design and fiber routing patterns based on an optical shape sensing fiber inserted and removed through a sewn-in channel in the suit.

FIG. 3 illustrates schematically an example suit design and fiber routing pattern based on optical shape sensing fiber inserted and removed through a sewn-in channel in the suit. The example design on the left includes a vertical launch vector orientation, and the example design on the right includes a horizontal launch vector orientation. Note that the fiber sensors are configured to traverse joint areas at a relatively sharp angle from the fiber path on both sides of the joint (e.g., leading up to and extending away from the joint). In addition, for some joints, e.g., the shoulder, the fiber may traverse the top of the shoulder as shown on the right side of FIG. 3 or under the shoulder as shown on the left side of FIG. 3. Optional fixed endpoints for each fiber sensor are also illustrated. Other fiber routing configurations could be used other than those shown.

Figure 4:
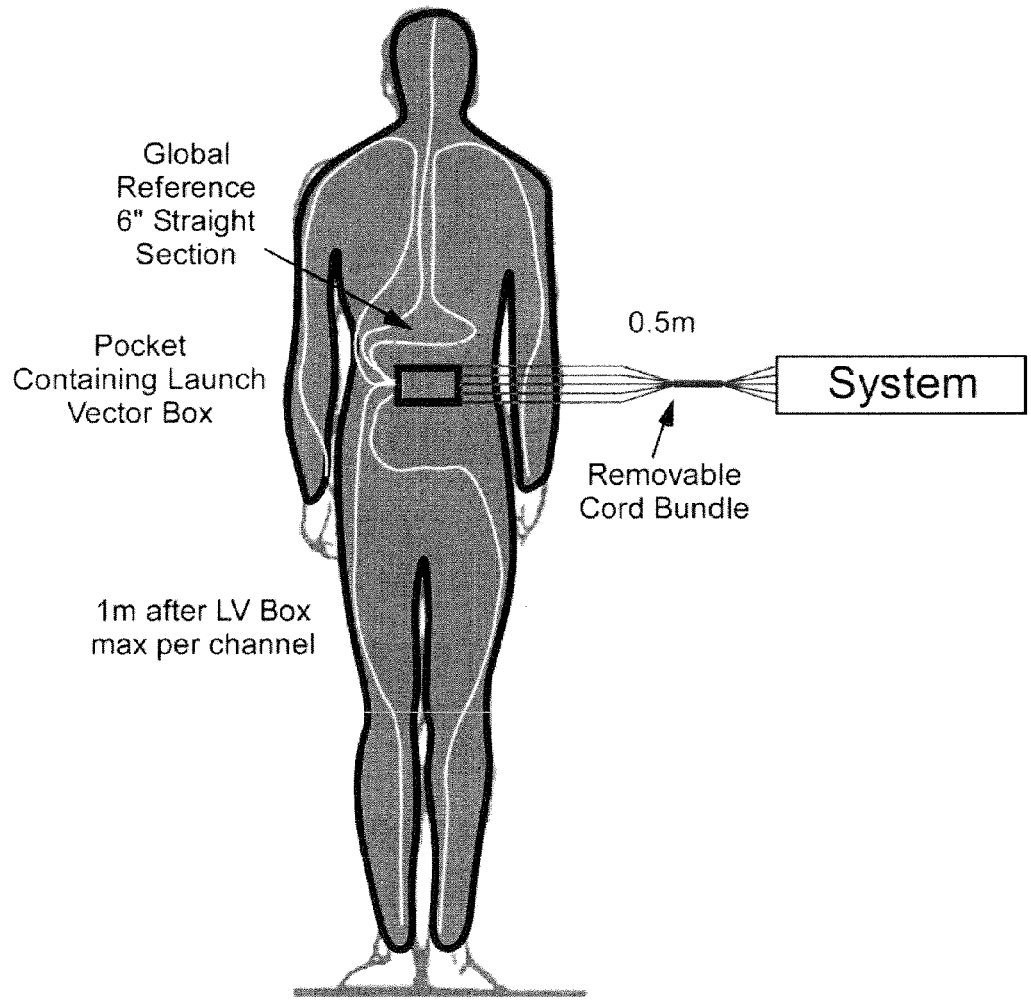
FIG. 4 shows schematically an example suit design with a pocket to protect the launch vector and prevent snagging along with connections to the data acquisition system.

FIG. 4 shows schematically an example suit design with a pocket to protect the launch vector and prevent snagging along with connections to the data acquisition system. Also shown is a section that can be integrated in a GPS unit with an IMU for global reference. The measured shape will be relative to this initial launch vector, and the GPS/IMU combination will allow the output of the shape sensing system to be orientated relative to the test environment through which the user moves and changes posture within.

Figure 5:
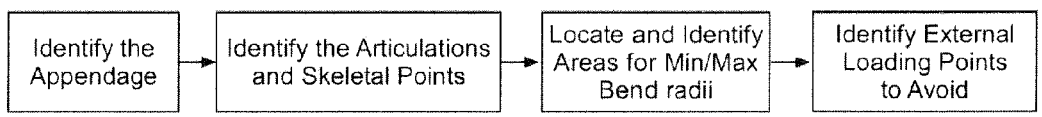
FIG. 5 is a flow type block diagram showing example criteria to consider in making a functional design.

A design of an example functional human-shaped body suit is now described. Again, the described technology is applicable to other types of bodies or shapes with appendages and joints. While it may appear that many paths are possible in the routing of the sensor into a wearable suit, it was discovered that in order to accommodate the functionality of the shape interrogation system, the sensor is preferably restricted to a path that meets certain criteria. One such path includes spirally winding around each appendage. A spiral path, however, presents significant problems as a body-subject flexes their muscles. A spiral path also requires a more difficult calibration and instrumentation plan in order to fit different sized body subjects. Criteria that must be considered to make a functional design and the decision process are shown in the process block diagram shown in FIG. 5. However, other types of fiber sensor paths may be used that meet these or other suitable criteria.

First, the appendage is identified which has both a given length and circumference and one determines a required length of the sensing fiber required to provide adequate sampling density. Second, articulation and skeletal points are identified to restrict the available paths as these positions must be substantially traversed across the joint to minimize the effects of pistoning during articulation of the appendage. Third, this fiber sensor path may be further restricted by the shape sensing system which has minimum bend radius that can be used in the routing of the sensor. A shape sensing system has a defined bend strain range that can be measured. A tighter bend radii results in higher bend strain signals. Moreover, the path may further be limited based on external loading points that may arise in a particular application or use case.

Figure 6A:
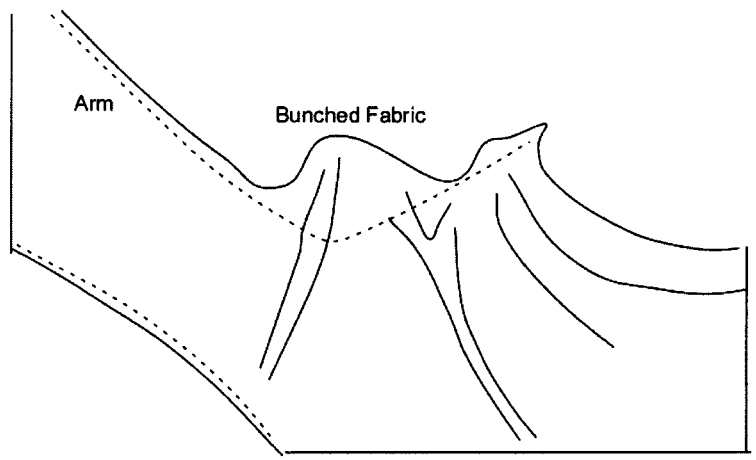
FIGS. 6A and 6B show examples of routing a shape sensor directly across a joint.
Figure 6B:
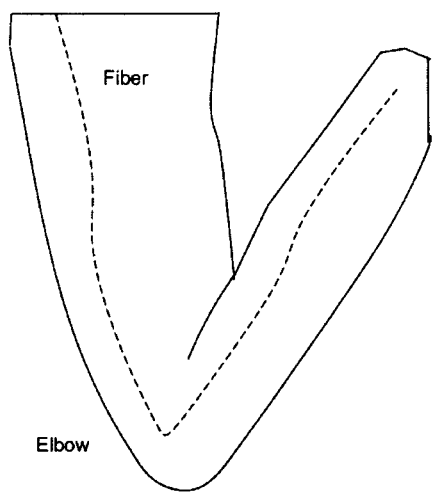
Figure 7A:
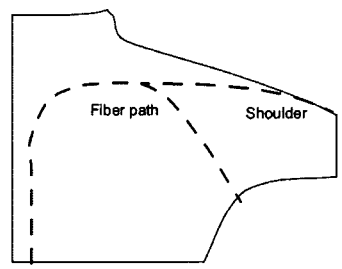
FIGS. 7A and 7B show an example of traversing a joint to remove the bend radius restrictions.
Figure 7B:
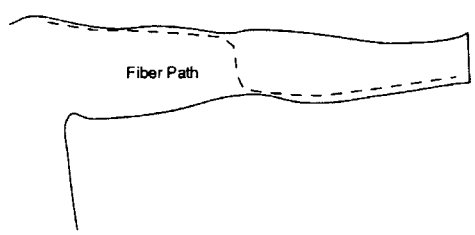

Examples of routing a shape sensor directly across a joint are shown in FIGS. 6A and 6B. This approach may be applied to all points on the suit in which pivotable articulation (e.g., bends) may occur. Bunching as a result of the piston effect is shown in FIG. 6A, and bunching at the elbow joint shown in FIG. 6B shows the potential for a tight bend radius. Traversing joints horizontally was found to be particularly advantageous for accuracy and reliability of the shaping sensing. In other words, the fiber in the suit is routed substantially parallel to the appendages (i.e., substantially parallel to the longitudinal axis of the body suit portion ("sleeve") designed to cover the appendages) but crosses the joint region at least partially transverse to the appendages (i.e., at least partially transverse to the longitudinal axis of the body suit sleeve). FIGS. 7A and 7B show an example of a fiber routing pattern that traverses a joint region transversely to remove the bend radius restrictions. The traversal results in a twist that does not cause the fiber to move laterally, thereby preserving the measurement location.

Figure 8:
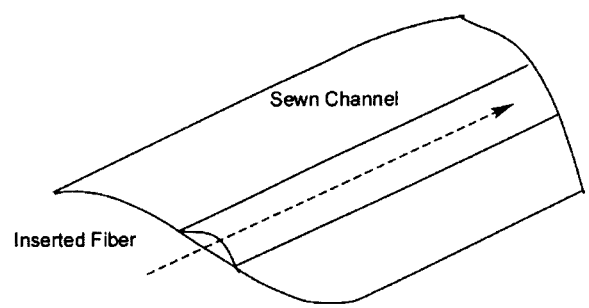
FIG. 8 shows an example channel design for the fiber to be instrumented into a suit.

Example installation and removal of sensors in and from a suit is now described. One useful feature of one example embodiment of the suit is the ability to remove the fiber optic sensors for the washing of the suit or if sensors need to be replaced. This can be accomplished by providing a sewn path, either in the form of a sewn tube, channel, or other structure that guide the sensor through the designed points. The sensor can be designed with a feature on the distal end to accept a pull string to aid in the installation. FIG. 8 shows an example channel design for the fiber to be instrumented into a suit. The channel is formed so as to define the designed sensor path and hold the sensor close to the body, thereby enabling the measurement.

Figure 9:
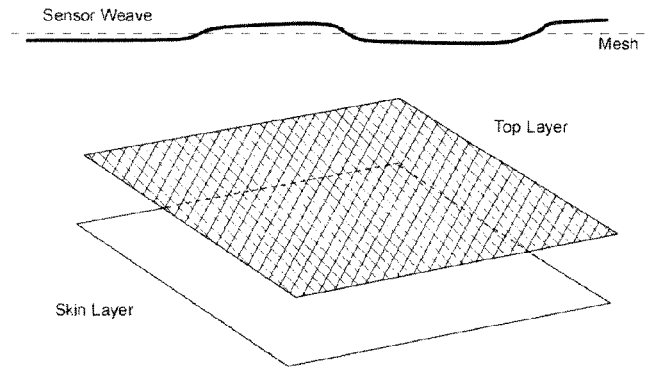
FIG. 9 shows a mesh example for a mesh suit embodiment.
Figure 10:
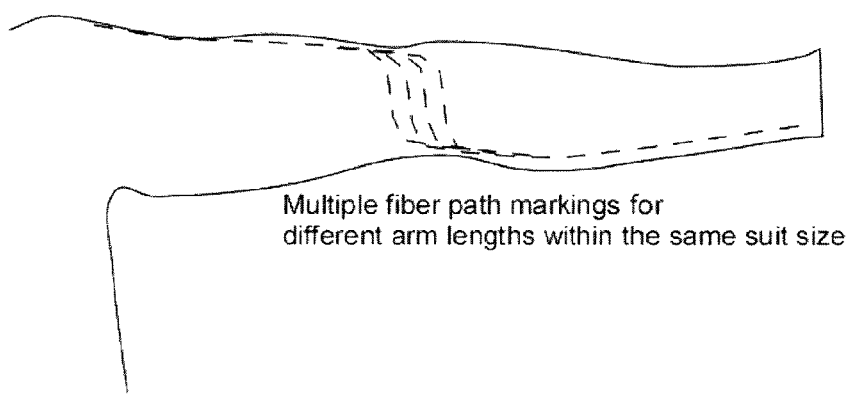
FIG. 10 shows an example multiple routing path markings for an elbow joint.

An alternative embodiment that can increase manufacturability and add functionality is the construction of the suit in two layers. The first layer, which is against the body, is manufactured from spandex or a similar lightweight and breathable yet form fitting material with significant stretching properties. This first layer determines the base size of the suit (e.g., small, medium, large). Using the same, or a slightly smaller pattern, a mesh is used to form the outer layer. The mesh is preferably sized such that the sensor can be woven easily through the holes, thereby reducing instrumentation time. As one example, having the mesh the same size enables the sensor to be held tightly against the body reducing the potential error. Mesh lines may be screen-printed or marked using a suitable method along the path. Multiple color coded lines may be used to show a user where the fiber needs to pass to make the measurement. This approach enables the same, large sized suit, to accommodate bodies with differing physiology. A mesh example is shown in FIG. 9, and an example routing path markings traversing an elbow joint in FIG. 10. These multiple fiber routing patterns provide flexibility for a same size garment for different bodies in order to increase the accuracy of fiber placement.

Figure 11:
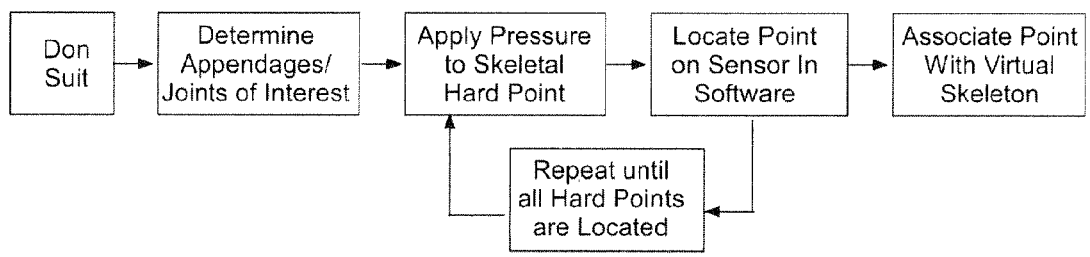
FIG. 11 is a flowchart diagram showing example steps for calibrating the suit and locating fiber sensors.

FIG. 11 is a flowchart diagram showing example steps for calibrating the suit and locating fiber sensors. The calibration defines the position in space of the suit relative to a global coordinate system. The user (e.g., a human subject) begins by donning an instrumented suit or donning a suit and then installing the sensors. Thereafter, an acquisition channel of the shape acquisition system is selected corresponding to an appendage to be calibrated. A point pressure is then applied at a location on the appendage at which the fiber is routed. This point pressure is measured as a localized strain by the shape sensing system. The point pressure on the appendage is then correlated to the corresponding point on the virtual skeleton reconstructed by the shape sensing system or noted manually for post data evaluation. This process is repeated for several points on each appendage for a given fiber optic sensor and each fiber optic sensor in the suit.

Figure 12:
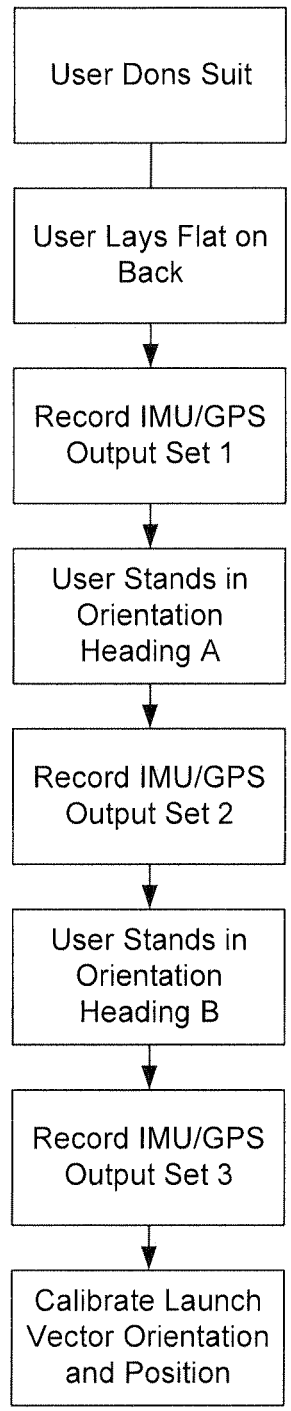
FIG. 12 is a flowchart diagram showing example steps for orientating a global (lab) frame with the output of an IMU.

FIG. 12 is a flowchart diagram showing non-limiting and example steps for allowing measurement of the sensor-integrated suit to be coordinated to a global (e.g., a lab) frame through the use of an IMU and GPS system. Fiber optic shape-sensing measurements are oriented relative to a coordinate frame determined by the cross-section of the fiber at the start location of the measurement, known as the launch region. Thus, when the launch region is tilted or rolled, the measured shape coordinates also rotate. To allow the user to freely move in an environment, it is desired to have this initial launch region of the shape coordinates to be orientated to the global frame.

In order to orient the measured coordinates instead to a fixed laboratory frame, an inertial measurement unit (IMU) can be affixed to the launch region. A calibration is performed to determine the relative orientation of the launch region to the principal axes of the IMU, but this calibration need only be performed once if this relative location is fixed. The use of the GPS system also allows the position of the launch region, not just its orientation, to be identified in the global lab frame.

In an example calibration of the global reference frame, a measured shape-sensing fiber is placed in a level horizontal plane, with the launch region pointing along the desired heading reference direction. The measured shape-sensing coordinates may be adjusted using a rotation matrix to ensure that the measured shape lies in the desired orientation. The parameters of this rotation matrix are then stored in a calibration file in memory. The IMU is then affixed to the launch region and also leveled and aligned to the desired heading reference direction. Once the shape measurement and IMU are oriented correctly, a tare is taken on the IMU, ensuring that all subsequent IMU measurements are relative to the calibration plane. In subsequent measurements, the calibrated rotation matrix is adjusted using orientation measurements from the IMU and applied to the coordinates of the shape-sensing measurement.

To calibrate the output of a shape sensing suit, the previous example can be expanded to allow the measured shape sensing suit to be orientated in a global frame. As shown in FIG. 12, the user would first put on a sensor integrated suit. The user would lay flat on the ground placing the IMU/GPS device as close to the floor surface as possible. The output of both the shape sensing system and IMU/GPS system are recorded and saved in memory. The user could then stand facing a known heading. As an example, a user could place their back against one wall of a corner. The outputs of the IMU/GPS device and shape sensing system are once again recorded and saved in memory. Lastly, the user may stand in a second known orientation. In this example case, the second wall of the corner may now be used providing a heading 90 degrees rotated from the previous standing case. The outputs of the three positions of the user may be used to orientate the IMU/GPS outputs to the global frame in which the user will use the suit. Since the IMU/GPS is collocated with the launch region of the shape sensing system, it is known that the output data of the shape sensing system begins with this same position and orientation.

Figures 13A, 13B:
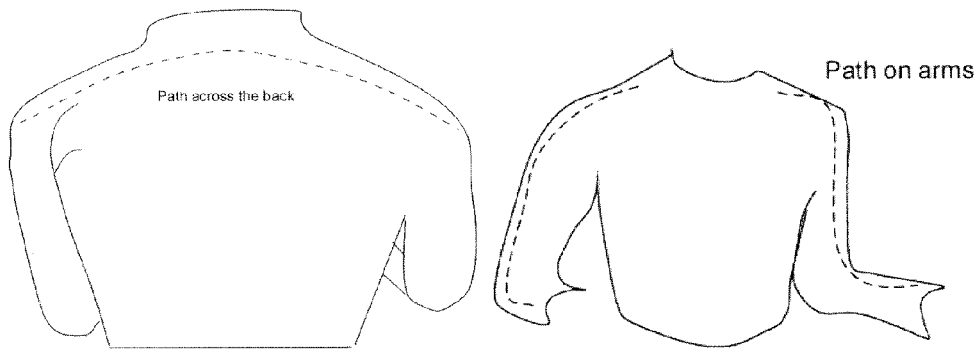
FIGS. 13A and 13B show example fiber sensor paths in a shirt portion of a test suit.

Testing of a prototype suit on a mannequin called "Gen-0" is now described. In a "Gen-0" test suit, a straight path for the fiber beginning at the right arm, moving straight up the arm and across the back, and then proceeding down the left arm was sewn. Example paths are shown in FIGS. 13A and 13B. For the Gen-0 trousers, a straight channel up the outside of each leg was formed.

Figure 14:
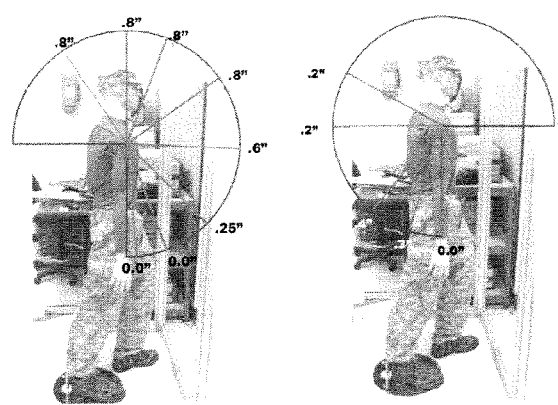
FIG. 14 illustrates initial test data showing the magnitude at which the piston effect and bend radii will occur as a human donning a test suit went through simple motions.

Initial testing showed the magnitude at which the piston effect and bend radii will occur as a human donning the suit went through simple motions. FIG. 14 shows Gen-0 being moved through a standard range of motions with the piston effect measured at each location. The test data in FIG. 14 shows that the sensor moving a distance on the order 1.5-2 inches for an arm moving through a simple motion. Unfortunately, this distance results in a large error for both body shape and posture as the index of the fiber that would be associated with, for example, the elbow moves in space while the elbow is not bending.

Figure 15:
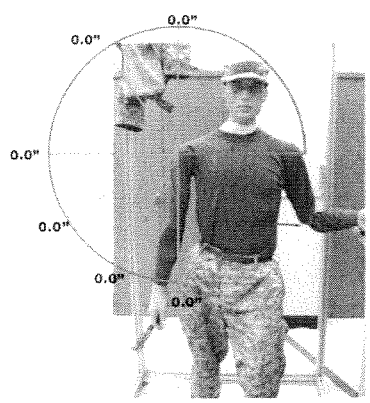
FIG. 15 illustrates test data with an improved fiber routing pattern that avoids pistoning effects and bend radii issues noted in FIG. 14.
Figure 15:
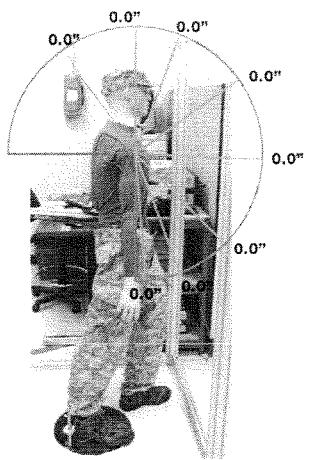
Figure 15:
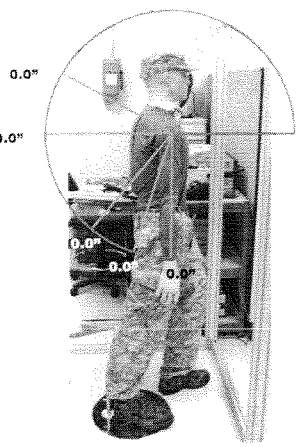

Thereafter, the fiber was fixed at a point on the test mannequin's back and decimations applied on the distal end of the sensor. At each position, the scale on the sensor was read to determine the amount that the fiber sensor was protruding or had been pulled back into the channel. An improved routing pattern was designed and applied to the suit and the test repeated. FIG. 15 shows test from FIG. 14 repeated with the improved fiber routing applied to the suit by traversing the fiber across the joints substantially transversely which removed nearly all of the undesirable fiber movement. In other words, as can be seen in FIG. 15, the effect of the pistoning is substantially and sometimes all removed when the sensor path is chosen such that articulation joints are traversed substantially transversely by the fiber, i.e., substantially transverse to the fiber path along the appendage.

Upon completion of static testing, the suit was tested dynamically with a cyclist wearing the suit and riding an indoor bicycle trainer. Testing in which a single channel (appendage) in the suit was instrumented was conducted. The cyclist proceeded through a series of movements and speeds during which data was collected.

Figure 16:
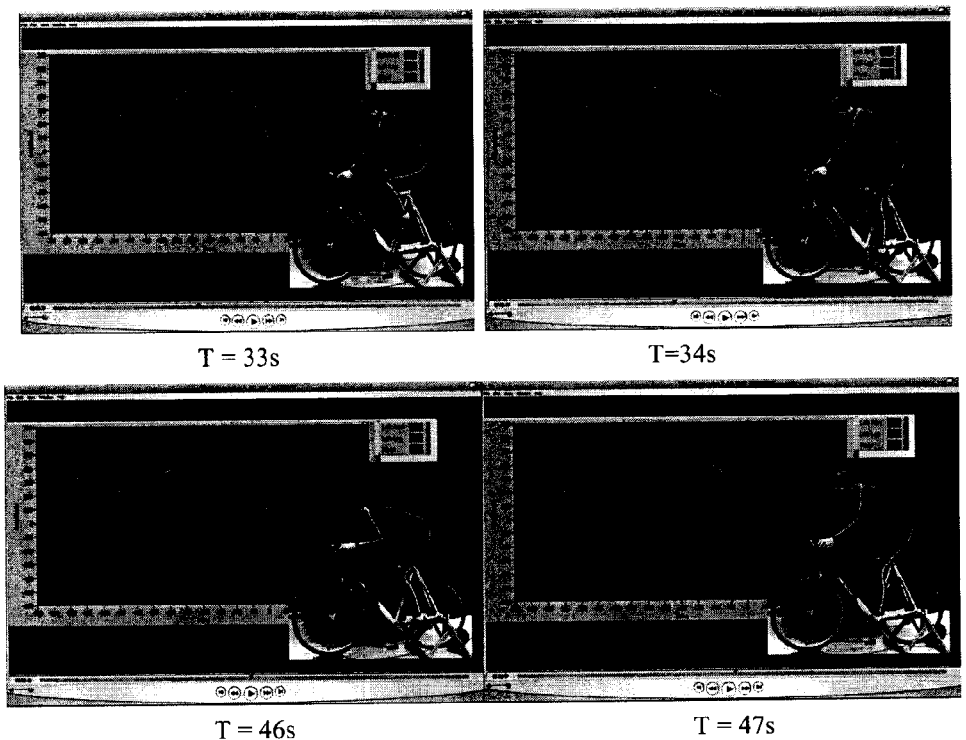
FIG. 16 shows data from a bent arm and a bent leg portion of two successive tests where the cyclist moves and data from two independent channels are used to measure the shape of the body.

In an example practical (but non-limiting) application, the data acquisition system includes five channels to accommodate human appendages of two arms, two legs, and a head. Test data from the sensors provided by the shape sensing system may be integrated into a single display. For the test, the cyclist repeated the movements three times with a different appendage instrumented for each trial. Data was acquired by the shape sensing system to produce the composite image shown in FIG. 16. FIG. 16 shows data from a bent arm and a bent leg portion of two successive tests where the cyclist moves and data from two independent channels are used to measure the shape of the body. The lower trace represents the leg, the upper trace represents the back and the head, and the middle trace corresponds to the arm. Times for 33 and 34 seconds show the progression of the leg as the cyclist pedals, and times 46 and 47 seconds show the bending of the arm.

In terms of accuracy, the fiber sensors performed well throughout all component and system level testing, meeting the expected performance requirements. For example spatial position tests, accuracy was demonstrated to be 1.6%. Relative angle accuracy was demonstrated to 1.3°, and absolute angle accuracy was demonstrated to 1.1° compared against a Faro Arm making the same measurements. These accuracy results for the example test were reported at 95% confidence level ($2\sigma$).

Testing of the accuracy of spatial position and the relative and absolute angle measurements was completed by placing the suit on a mannequin and installing a sensor into one of the limbs. Test matrices were defined to exercise the full range of motion of major joints per MIL-STD-1472G TABLE XXXVI. An example of the test matrices are shown in FIGS. 17A and 17B.

The shoulder and hip joints were the least representative of a human's on the mannequin and their limitations affected the test plan. Each of these was set up as two independent rotational joints as opposed to the biometrically accurate ball joint. An out of plane bend to locate the hand away from the side and out in front of the mannequin was done by rotating each of the two joints.

Figure 18:
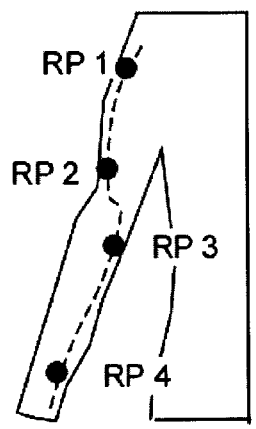
FIG. 18 shows each reference point (RP) and its placement on the arm.

For each data set, the mannequin was moved to a vertical "attention" position with its arm at its side. The arm was then moved into the desired position, the sensor located, and a measurement taken with the fiber optic data acquisition system and the Faro Arm. Spheres were placed onto the sensors to provide the measurement reference for the Faro Arm. FIG. 18 shows each reference point (RP) and its placement on the arm.

Figures 19A, 19B:
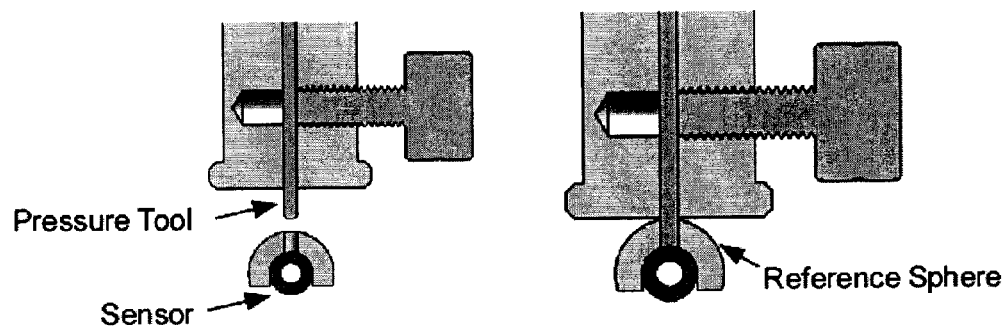
FIGS. 19A and 19B show an example index location tool use with reference target installed onto sensor.

It was necessary to determine the index location on the sensor to correlate the position measurements. A "touch-to-locate" method was employed in which a special tool is inserted into the hole on the sphere. The tool applies a point pressure to the sensor which can be used to determine the exact point on the sensor the measurement is being taken. FIGS. 19A and 19B show an example index location tool use with reference target installed onto sensor.

Spatial Position, relative angle, and absolute angle data were taken simultaneously during the test. Each measurement was repeated 9 times to add statistical significance to the datasets and reach the 95% confidence in the uncertainty. In between each measurement the arm was relaxed to attention. Examples of the test results are shown below in Tables 1A and Table 1B:

TABLE 1A

Spatial position, RP1/5 (error in millimeters)

| Test angle | mean error | standard deviation | 95% α (±) | error, % length |
|---|---|---|---|---|
| A1.a | 9.46 | 1.21 | 2.36 | 0.64 |
| A1.b | 10.75 | 1.22 | 2.38 | 0.72 |
| A1.c | 16.03 | 0.82 | 1.60 | 1.08 |
| A2.a | 12.34 | 1.14 | 2.22 | 0.83 |
| A2.b | 11.79 | 1.57 | 3.06 | 0.79 |
| A2.c | 10.73 | 0.96 | 1.87 | 0.72 |
| E1.a | 16.99 | 1.81 | 3.53 | 1.15 |
| E1.b | 14.25 | 1.95 | 3.80 | 0.96 |
| E1.c | 12.47 | 0.90 | 1.76 | 0.84 |
| H1.a | 14.75 | 3.84 | 7.49 | 1.16 |
| H1.b | 10.64 | 5.39 | 10.51 | 0.83 |
| H1.c | 15.88 | 1.04 | 2.03 | 1.07 |
| H2.a | 13.74 | 5.32 | 10.37 | 0.93 |
| H2.b | 17.28 | 1.52 | 2.96 | 1.16 |
| H2.c | 15.58 | 1.60 | 3.12 | 1.05 |
| H5.b | 12.91 | 1.04 | 2.03 | 0.87 |
| H5.c | 14.78 | 0.92 | 1.79 | 0.99 |
| F2.a | 14.75 | 1.88 | 3.67 | 0.99 |
| F2.b | 15.51 | 0.97 | 1.89 | 1.05 |
| F2.c | 15.88 | 1.04 | 2.03 | 1.07 |

TABLE 1B

Spatial position, RP2/6 (error in millimeters)

| Test angle | mean error | standard deviation | 95% α (±) | error, % length |
|---|---|---|---|---|
| A1.a | 11.21 | 1.70 | 3.32 | 0.70 |
| A1.b | 9.41 | 1.20 | 2.34 | 0.59 |
| A1.c | 16.23 | 1.29 | 2.52 | 1.01 |
| A2.a | 13.28 | 1.14 | 2.22 | 0.83 |
| A2.b | 12.66 | 1.88 | 3.67 | 0.79 |
| A2.c | 12.15 | 0.98 | 1.91 | 0.76 |
| E1.a | 18.38 | 2.27 | 4.43 | 1.15 |
| E1.b | 15.69 | 2.22 | 4.33 | 0.98 |
| E1.c | 13.33 | 1.09 | 2.13 | 0.83 |
| H1.a | 18.20 | 4.97 | 9.69 | 1.22 |
| H1.b | 16.37 | 8.43 | 16.44 | 1.10 |
| H1.c | 14.33 | 1.13 | 2.20 | 0.89 |
| H2.a | 18.04 | 6.90 | 13.46 | 1.13 |
| H2.b | 20.42 | 2.01 | 3.92 | 1.27 |
| H2.c | 16.91 | 2.50 | 4.88 | 1.05 |
| H5.b | 13.57 | 1.00 | 1.95 | 0.85 |
| H5.c | 15.56 | 1.42 | 2.77 | 0.97 |
| F2.a | 15.84 | 3.86 | 7.53 | 0.99 |
| F2.b | 15.40 | 1.26 | 2.46 | 0.96 |
| F2.c | 14.33 | 1.13 | 2.20 | 0.89 |

Figure 20:
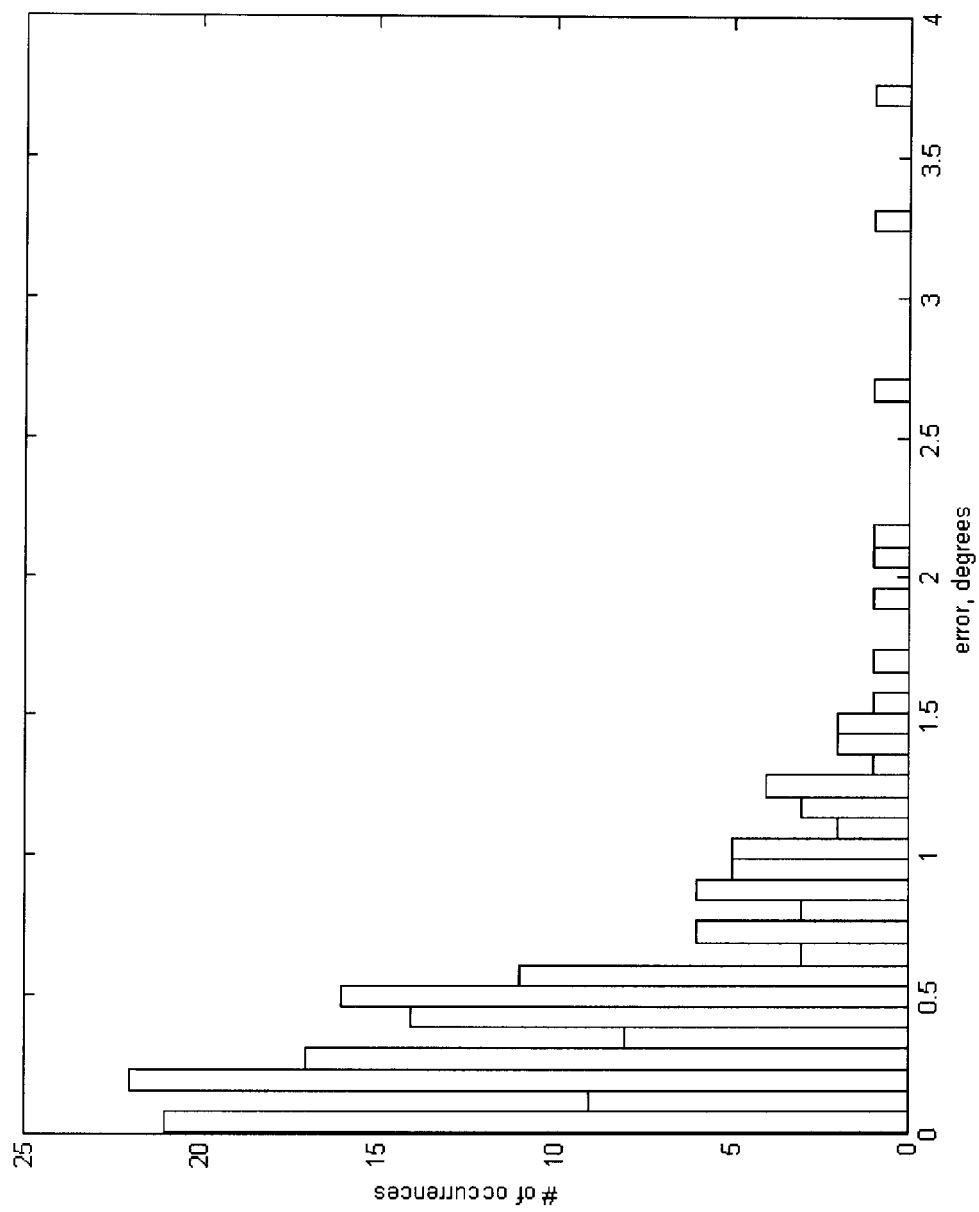
FIG. 20 is a bar graph an example relative test angle results distribution.

FIG. 20 is a bar graph the example relative test angle results distribution.

The technology describes an instrument which includes a bodysuit integrated with optical fiber to measure the position, shape, and posture of a subject. The fiber is advantageously routed across joints on the suit to minimize error from changing positions of the fiber relative to the joint locations. The fiber is also advantageously routed to reduce or minimize the bend radii which may cause failures. The example embodiments above describe an instrumented suit for human performance assessment, gear evaluation, and graphic motion capture. The suit and technology may be applied to articulated appendages and to any device that is moved and can have a fabric cover applied. For example, a suit may be designed to fit over an articulated robotic arm, e.g., controlled via a robotic interface or through a feedback loop with a human directing each step. The suit data provides a valuable form of feedback for operators in many fields including civil structure construction and autonomous robotics. Additionally, suits may be designed for animal testing, monitoring, and evaluation. For service animals and military applications this could enable posture and positional knowledge to be passed on to the handlers about the animals' current state. The described angular measurement with respect to a global plane can also be applied to survey equipment in obstructed view cases such as foliage, cityscapes, and adverse weather.

The above description sets forth specific details, such as particular embodiments for purposes of explanation and not limitation. But it will be appreciated by one skilled in the art that other embodiments may be employed apart from these specific details. In some instances, detailed descriptions of well known methods, nodes, interfaces, circuits, and devices have been omitted so as not obscure the description with unnecessary detail. Those skilled in the art will appreciate that the functions described may be implemented in one or more nodes using optical components, electronic components, hardware circuitry (e.g., analog and/or discrete logic gates interconnected to perform a specialized function, ASICs, PLAs, etc.), and/or using software programs and data in conjunction with one or more digital microprocessors or general purpose computers. Moreover, certain aspects of the technology may additionally be considered to be embodied entirely within any form of computer-readable memory, such as solid-state memory, magnetic disk, or optical disk containing an appropriate set of computer instructions that would cause a processor to carry out the techniques described herein.

Although the description above contains many specifics, those specifics should not be construed as limiting but as merely providing illustrations of some presently preferred embodiments. The technology fully encompasses other embodiments which may become apparent to those skilled in the art. Reference to an element in the singular is not intended to mean "one and only one" unless explicitly so stated, but rather "one or more." All structural and functional equivalents to the elements of the above-described embodiments that are known to those of ordinary skill in the art are expressly incorporated herein by reference and are intended to be encompassed hereby. Moreover, it is not necessary for a device or method to address each and every problem sought to be solved by the described technology for it to be encompassed hereby.

The invention claimed is:

1. Measurement apparatus comprising:
    a body suit for a body that includes an appendage having a pivotable joint, the body suit comprising a sleeve to cover the appendage, wherein a first portion of the sleeve is configured to cover the pivotable joint,
    one or more multi-core optical fiber sensors within or on the sleeve in a routing pattern that is substantially aligned with a longitudinal axis of the sleeve except within the first portion where the routing pattern within the first portion is substantially transverse to the longitudinal axis of the sleeve; and
    an optical shape sensing system coupled to the one or more multi-core optical fiber sensors and configured to send light into the one or more multi-core optical fiber sensors and determine a position of each of the multiple appendages based on reflected optical signal measurements detected from one or more multi-core optical fiber sensors.

2. The measurement apparatus in claim 1, wherein the optical shape sensing system is configured to determine a shape of the body based on reflected optical signals detected from one or more multi-core optical fiber sensors.

3. The measurement apparatus in claim 1, wherein the optical shape sensing system is configured to determine a posture of the body based on reflected optical signals detected from one or more multi-core optical fiber sensors.

4. The measurement apparatus in claim 1, wherein the optical shape sensing system is an optical frequency-domain reflectometry (OFDR) based system.

5. The measurement apparatus in claim 1, further comprising a launch unit coupled to a first end of each of the one or more multi-core optical fiber sensors, wherein an orientation of the launch unit defines a coordinate frame for the optical shape sensing system measurements.

6. The measurement apparatus in claim 5, wherein the launch unit includes or is coupled to an inertial measurement unit (IMU).

7. The measurement apparatus in claim 5, wherein the launch unit includes or is coupled to a global positioning system (GPS).

8. The measurement apparatus in claim 1, wherein the one or more multi-core optical fiber sensors is configured in or on the body suit to traverse across the one or more movable joints from a first side of the one or more movable joints to a second opposing side of the one or more movable joints.

9. The measurement apparatus in claim 1, wherein the one or more multi-core optical fiber sensors is configured in or on the body suit to traverse across the one or more movable joints with a predetermined, minimum bend radius associated with the one or more multi-core optical fiber sensors.

10. The measurement apparatus in claim 1, wherein the optical shape sensing system is configured to calibrate measurements detected from the one or more multi-core optical fiber sensors as configured in or on the body suit.

11. Measurement apparatus comprising:
  a body suit for a body that includes an appendage having a pivotable joint, the body suit comprising a sleeve to cover the appendage, wherein a first portion of the sleeve is configured to cover the pivotable joint;
  one or more multi-core optical fiber sensors within or on the sleeve in a routing pattern that is substantially aligned with a longitudinal axis of the sleeve except within the first portion and that is at least partially transverse to the longitudinal axis within the first portion;
  a connection terminal configured to connect the one or more multi-core optical fiber sensors to an optical shape sensing system for sending light into the one or more multi-core optical fiber sensors and determining a position of each of the multiple appendages based on reflected optical signal measurements detected from the one or more multi-core optical fiber sensors; and
  a launch unit coupled to a first end of each of the one or more multi-core optical fiber sensors, wherein an orientation of the launch unit defines a coordinate frame for the optical shape sensing system measurements.

12. The measurement apparatus in claim 11, wherein the launch unit includes or is coupled to an inertial measurement unit (IMU).

13. The measurement apparatus in claim 11, wherein the launch unit includes or is coupled to a global positioning system (GPS).

14. The measurement apparatus in claim 11, wherein the one or more multi-core optical fiber sensors is configured in or on the body suit to traverse across the one or more movable joints from a first side of the one or more movable joints to a second opposing side of the one or more movable joints.

15. The measurement apparatus in claim 11, wherein the one or more multi-core optical fiber sensors is configured in or on the body suit to traverse across the one or more movable joints from a first side of the one or more movable joints to a second opposing side of the one or more movable joints.

16. The measurement apparatus in claim 11, wherein the one or more multi-core optical fiber sensors is configured in or on the body suit to traverse across the one or more movable joints with a predetermined, minimum bend radius associated with the one or more multi-core optical fiber sensors.

17. The measurement apparatus in claim 11, wherein the body is a human body, an animal body, or a robotic body.

18. A method for making a body suit for a body that includes an appendage having a pivotable joint, the body suit comprising a sleeve to cover the appendage, wherein a first portion of the sleeve is configured to cover the pivotable joint, the method comprising:
  routing one or more multi-core optical fiber sensors within or on the sleeve in a routing pattern that is substantially aligned with a longitudinal axis of the sleeve except within the first portion and that is at least partially transverse to the longitudinal axis within the first portion,
  providing a connection terminal that is configured to connect the one or more multi-core optical fiber sensors to an optical shape sensing system for injecting light into the one or more multi-core optical fiber sensors and determining a position of one or more of the multiple appendages based on reflected optical signal measurements detected from one or more multi-core optical fiber sensors, and
  coupling a launch unit to a first end of each of the one or more multi-core optical fiber sensors, wherein an orientation of the launch unit defines a coordinate frame for the optical shape sensing system measurements.

* * * * *